US010646364B2

(12) United States Patent
Dakak

(10) Patent No.: US 10,646,364 B2
(45) Date of Patent: May 12, 2020

(54) CATHETER

(71) Applicant: Nadar A. Dakak, Potomac, MD (US)

(72) Inventor: Nadar A. Dakak, Potomac, MD (US)

(*) Notice: Subject to any disclaimer, the term of this patent is extended or adjusted under 35 U.S.C. 154(b) by 242 days.

(21) Appl. No.: 15/019,183

(22) Filed: Feb. 9, 2016

(65) Prior Publication Data

US 2017/0319365 A1    Nov. 9, 2017

(51) Int. Cl.
| | |
|---|---|
| *A61F 2/95* | (2013.01) |
| *A61F 2/954* | (2013.01) |
| *A61M 25/10* | (2013.01) |
| *A61M 25/01* | (2006.01) |
| *A61M 25/09* | (2006.01) |
| *A61F 2/90* | (2013.01) |
| *A61F 2/958* | (2013.01) |
| *A61F 2/966* | (2013.01) |
| *A61F 2/82* | (2013.01) |

(52) U.S. Cl.
CPC .............. *A61F 2/954* (2013.01); *A61F 2/90* (2013.01); *A61F 2/958* (2013.01); *A61F 2/966* (2013.01); *A61M 25/0108* (2013.01); *A61M 25/09* (2013.01); *A61M 25/104* (2013.01); *A61M 25/10182* (2013.11); *A61F 2002/821* (2013.01)

(58) Field of Classification Search
CPC .......... A61F 2/954; A61F 2/966; A61F 2/958; A61F 2002/9583; A61F 2/962; A61F 2/90; A61F 2002/821; A61M 25/104; A61M 25/10182; A61M 25/0108; A61M 25/09

See application file for complete search history.

(56) References Cited

U.S. PATENT DOCUMENTS

| | | | |
|---|---|---|---|
| 5,607,444 A | 3/1997 | Lam | |
| 5,984,946 A * | 11/1999 | Gupta | A61M 25/04 606/194 |
| 7,402,168 B2 * | 7/2008 | Sanderson | A61F 2/915 604/101.01 |
| 2006/0155363 A1 * | 7/2006 | LaDuca | A61F 2/856 623/1.16 |
| 2007/0173784 A1 | 7/2007 | Johansson et al. | |
| 2007/0270935 A1 | 11/2007 | Newhauser et al. | |
| 2008/0086083 A1 | 4/2008 | Towler | |
| 2008/0208307 A1 | 8/2008 | Ben-Muvhar et al. | |
| 2008/0243233 A1 * | 10/2008 | Ben-Muvhar | A61F 2/954 623/1.35 |
| 2009/0043194 A1 | 2/2009 | Barbut | |
| 2014/0194920 A1 * | 7/2014 | Krahbichler | A61F 2/013 606/200 |

* cited by examiner

*Primary Examiner* — Erich G Herbermann

(74) *Attorney, Agent, or Firm* — Bradford E. Kile; Scott Houtteman; Houtteman Law LLC

(57) ABSTRACT

An angioplasty apparatus for facilitating accurate placement of a lumen stent for dilating a stenosis, the apparatus includes arcuate low pressure balloon segment(s) connected at a distal end of a guiding catheter with gap(s) to facilitate blood flow during a stenting procedure. Optimal positioning of a stent at a lumen bifurcation is facilitated to obviate any tendency of a stent to miss a proximal end of a stenosis branch lumen while concomitantly preventing the stent from protruding into an original lumen, such as a patient's aorta.

7 Claims, 5 Drawing Sheets

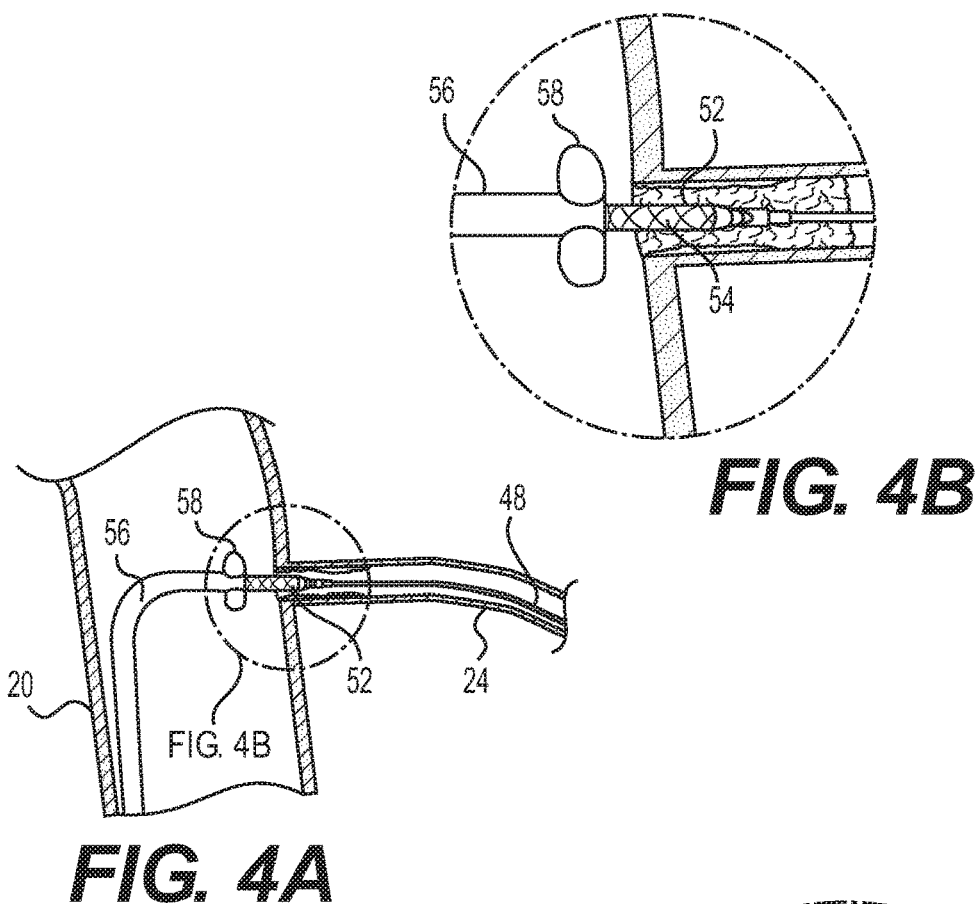
*FIG. 4B*
*FIG. 4A*
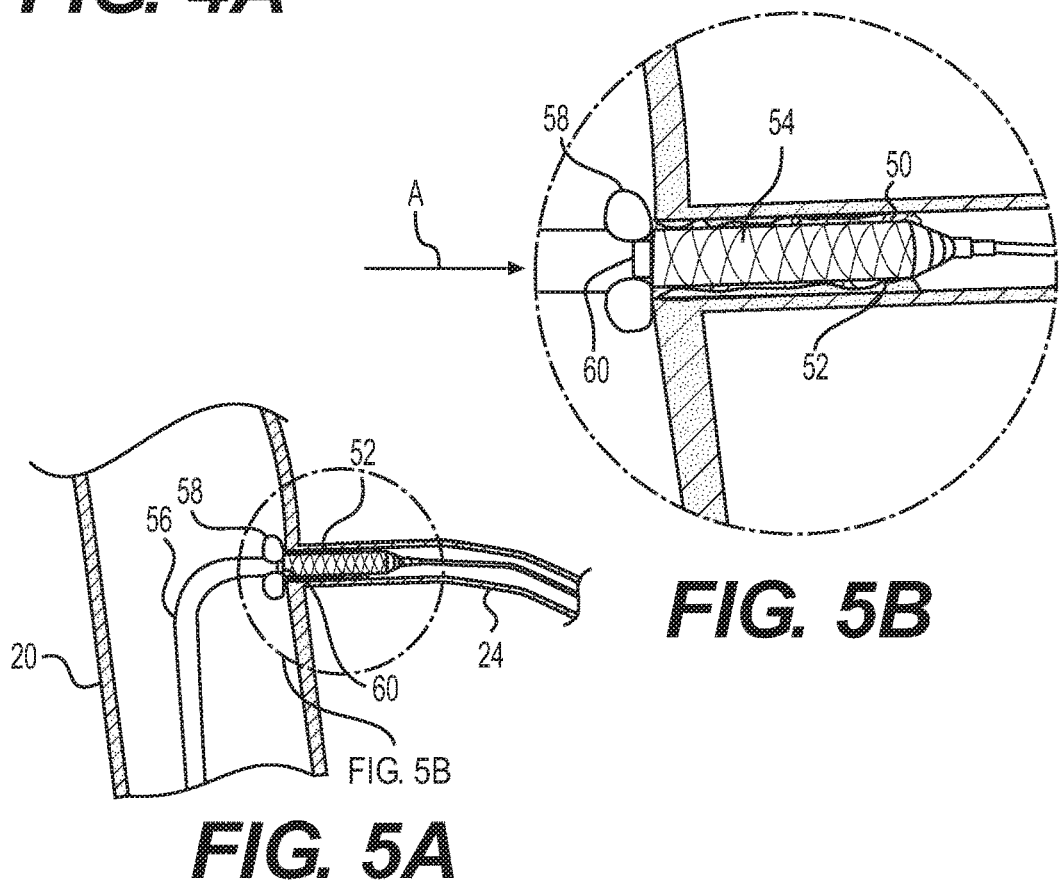
*FIG. 5B*
*FIG. 5A*

CATHETER

RELATED APPLICATION

This application relates to co-pending applications entitled "Angioplasty Anchor and/or Marker Balloon Stent Catheter Apparatus And Method" Ser. No. 15/019,207 and "Angioplasty, Self-Expanding, Stent Catheter With Low Pressure Anchor and/or Marker Balloon Assembly and Method" Ser. No. 15/019,237, both of common inventorship and ownership as the present application and as filed on an even date herewith. The disclosures of these co-pending applications are incorporated herein by reference as though set forth at length.

BACKGROUND OF THE DISCLOSURE

This invention relates to a marker and guide catheter in the field of coronary and peripheral angioplasty with stenting. More specifically, this invention relates to accurate stent placement when a stenotic segment is located at a lumen opening or bifurcation of a blood vessel.

The vascular bed in humans is a complex and extensive network of lumens carrying blood and delivering oxygen and nutrients throughout the skeletal network, organs and muscle tissues of the body. At a macro level the human circulatory system can be logically characterized as originating from the heart with an ascending aorta extending from the left ventricle upwardly into an arch and then descending generally vertically downward via a central lumen column through a patient's thoracic region and diaphragm to an abdominal aorta segment. The aorta terminates with common left and right iliac arteries extending into the common femoral arteries and down into lower extremities.

In general terms the aorta provides a base for systemic circulation for the entire body. Right and left coronary branches extend from an aortic root to supply a patient's heart while an aortic arch supplies blood to the patient's head, neck and arms. Branches from the thoracic aorta supply the chest and branches from the abdominal aorta supply the abdomen while the pelvis and lower extremities are fed from common iliac arteries extending from a base region of the aorta.

The human vascular system, originating from the heart, is composed of a series of flexible lumens decreasing in diameter and increasing in branches. In broad terms a sequence of blood flow is from a left heart ventricle to an aorta, to arteries, to arterioles, to venules, to veins, and to a vena cava back to a right side of the heart. Vascular lumens are composed of elastic tissue which can, over time, become somewhat hardened in a disease zone due to an internal accumulation of cholesterol laden plaques, which is a fatty material composed of cholesterol and other particles which build up within an artery wall to create a narrowing (stenosis) of the artery. Plaque stenotic segments can decrease vessel elasticity and concomitantly occlude a free flow of blood through the lumen. This malady is sometimes referred to as atherosclerotic arterial disease.

In 1964 an vascular radiologist by the name of Charles Dotter, often referred to as the "Father of Interventional Radiology" pioneered development of angioplasty and a catheter delivered stent as a treatment for peripheral arterial disease.

Stents are now universally used in percutaneous coronary and peripheral angioplasty procedures, which effectively open narrowed blood vessels. A stent is a tiny, expandable, cylindrical wire mesh scaffolding, mounted on a deflated balloon in a "crimped" or collapsed state. It is inserted into the narrowed segment of the artery over a thin angioplasty wire via a guide catheter and then expanded by inflating the balloon.

A guide catheter is a long hollow tube which is percutaneously advanced into an opening of a coronary artery or other arteries originating from the aorta. The guide catheter allows a percutaneous injection of contrast media into the stream of a blood vessel. A thin angioplasty guide wire is advanced, through the guide catheter, into a blood vessel and inserted through the narrowed lumen stenosis. A stent (with an interior, concentric, collapsed, tubular balloon) is introduced, over the angioplasty guide wire, through the guide catheter and accurately positioned at a lumen stenosis site. High pressure (nine to eighteen atmospheres) is then used to inflate the balloon and permanently expand the stent scaffolding outwardly to radially compress plaque at the lumen stenosis segment, making an enlarged opening inside the artery for improved blood flow. The stent balloon is thereafter deflated and withdrawn through the interior of the guide catheter along with the guide wire and the expanded wire stent remains positioned as scaffolding at the stenotic site.

An interventional physician uses radiography, an X-ray procedure to identify a stenosis location and estimates the size of a diseased blood vessel and severity of stenotic plaque narrowing. Blood vessels are not visible by X-ray per se, however, by injecting a contrast media (dye) through the guide catheter a trained physician is capable of accurately viewing arterial boundaries with the pulsating flow of blood through downstream arteries and develop an accurate sense of a stenotic vessel site requiring interventional correction.

Placing a stent at a site of a stenosis in a downstream segment of a blood vessel is now considered a routine process. When plaque stenosis narrowing is located at a bifurcation opening of the blood vessel from the aorta, or at a downstream bifurcation site where a blood vessel branches, however, optimal placement of the stent is more challenging. In this, positioning a stent too distal may miss part of a narrowing stenosis while positioning a stent too proximal may result in proximal end of the stent protruding into a primary blood vessel.

Examples of challenging locations are plaque stenosis occurring at an opening of arteries originating from the aorta: the left main coronary artery, the right coronary artery, the innominate artery, left common carotid artery, left subclavian artery, celiac artery, superior mesenteric artery, inferior mesenteric artery, the left and right renal arteries and iliac arteries. Other examples include vessel bifurcations downstream in the coronary arterial tree such as the left anterior descending and the left circumflex coronary arteries which bifurcate from the left main coronary artery. It also includes peripheral arteries such as the common femoral arteries bifurcations.

Due to the complexity of accurately positioning a stent at a vessel transition opening, in a pulsating circulatory system, stenting a stenosis at a bifurcation requires a longer operative time, exposing a patient and staff to extra radiation during the angiography, and injecting larger amounts of radiopaque contrast media which may compromise the patient's hemodynamic status and kidney functions. It is not uncommon for an interventional physician to use additional stents because of non-satisfactory initial results due to stent malposition. The procedure may therefore become prolonged and complex, carrying out higher risks and a higher rate of complications.

In order to address this problem it has been previously suggested to use a two part balloon stent catheter, where a relatively large torus part of a balloon is positioned at a proximal end of a cylindrical stent balloon. The inflated torus balloon serves as a stop at a bifurcation junction to prevent the stent on the cylindrical companion stent balloon from extending too far into a bifurcated lumen. At least one limitation of such a torus stop balloon, however, is that it will also temporarily limit or even occlude blood flow into the target blood vessel during the stent positioning. It will also block the contrast media (dye) from reaching the target vessel. The contrast media is needed to confirm the final positioning of the stent before the deployment.

To address and ameliorate the torus, stop balloon negative issues and address a desire for a more sophisticated and accurate stent placement at bifurcation junctions, the subject invention is directed to a smaller, low pressure (one or two atmospheres) arcuate marker balloon segment or segments located at a distal end of a guide catheter. The arcuate marker balloon segment or segments, will enable a free flow of blood. In addition the arcuate marker balloon will provides a specific identification of a bifurcation site to accurately position a conventional stent, using both angiography and tactile feedback, while reducing the use of contrast media.

When the stenosis is at the opening of the blood vessel, that branches from the aorta, the guide catheter is percutaneously advanced, stopping when the tip lands at an opening of the branching blood vessel. Contrast media is percutaneously injected via the guide catheter into the target vessel to view the anatomy. The angioplasty wire is then advanced in the target vessel through and past a stenotic site within the blood vessel. The stent apparatus is then advanced over the guide wire to the site of the stenosis at the opening of the blood vessel. The guide catheter tip is then pulled back into the aorta and a marker balloon segment or segments are expanded to allow stent positioning at the opening of the blood vessel.

The marker balloon segment or segments on a distal end of the guide catheter are percutaneously inflated via a small independent tube or tubes within the guiding catheter using contrast media. By the provision of angiography and tactile feedback, the guide catheter with the visible inflated marker balloon at its tip is gently advanced, to face the aortic wall and the opening of the branching blood vessel. The marker balloon segment or segments will stop the guide catheter from sliding into the branch, thus marking the aortic wall and the side branch opening. The balloon stent is then gently retracted until a radiopaque marker band on a proximal end of the balloon stent joins with the marker segment or segments on the distal end of the guide catheter as one visible radiopaque image thus indicating accurate position of the stent at a bifurcation junction of the vascular system juxtaposed at a distal end of the guide catheter marker balloon. This provides optimal positioning of the proximal edge of the balloon stent at the opening of the branching vessel. Final balloon stent position, before the stent balloon is inflated, may be confirmed by injection of contrast media via the guide catheter and past the guide catheter marker balloon segment or segments.

Inflation pressure for the arcuate marker balloon segment or segments at the distal end of the guide catheter is far less than the operating pressure of the stent balloon. While a stent balloon needs a special inflation device to reach pressures between nine and eighteen atmospheres, the subject arcuate balloon marker segment or segments are advantageously inflated to one or two atmospheres by a hand syringe. Moreover, a blood vessel wall may have a special geometry. A low pressure marker balloon arcuate segment or segments can advantageously be used to provide easier and better alignment with a main vessel wall by controlling the amount of pressure applied to a particular balloon segment.

In addition, a low pressure arcuate marker balloon segment or segments at a distal end of a guide catheter is operable to set or alter an angle of a guide catheter distal end, when inside the artery branching from the aorta, with respect to a subsequent branch lumen, to advantageously adjust the distal end angle to facilitate insertion of the angioplasty wire and a balloon stent at a difficult angle of a target blood vessel. Inflating the marker balloon within the branch lumen may also stabilize the guide catheter position without blocking the blood flow distally.

The arcuate shaped balloon segment or segments at a distal end of the guide catheter will prevent complete blocking of the blood flow when the guide catheter marker balloon or balloons are inflated. The subject marker balloon segment or segments at a distal end of the guide catheter also enables continuous monitoring of blood pressure in a patient's aorta. In this, aorta blood flowing past the low pressure marker balloon segment or segments allows measuring the aortic blood pressure, through the guide catheter tip.

The subject arcuate marker balloon segment or segments are connected to the tip of the guide catheter but do not extend a full three hundred and sixty degrees circumferentially around the distal end of the guide catheter. The arcuate shape of the subject low pressure marker balloon segment or segments will accommodate and accurately identify a wall location of the main blood vessel and opening of a side branch to the main vessel. The arcuate shaped segments, in contrast to a full circumferential configuration, will not occlude blood flow to a target vessel during a stenting procedure.

Further selective delivery of marker fluid pressure to a distal end of a guide catheter marker balloon segment or segments can be advantageously used to orient a distal end of a guide catheter with respect to an opening of a branch vessel. In a similar manner it can stabilize the position of the guide catheter in the primary vessel during complex angioplasties, while allowing continuous blood flow to the target vessel and continuous aortic pressure monitoring at the guide catheter tip.

The limitations suggested in the preceding are not intended to be exhaustive but rather are among many which may tend to reduce the effectiveness, reliability and patient satisfaction with prior guide catheter structures for angioplasty, with stenting, at bifurcation sites in a circulatory system. Other noteworthy problems may also exist; however, those presented above should be sufficient to demonstrate that present angioplasty, involving stenting at bifurcation sites in a circulatory system, appearing in the past will admit to worthwhile improvement.

THE DRAWINGS

Numerous advantages of the present invention will become apparent from the following detailed description of preferred embodiments taken in conjunction with the accompanying drawings wherein:

FIG. 4A is a side, partial cross-sectional view of a stent being placed at a renal artery bifurcation junction of the type depicted in FIG. 3;

FIG. 4B is a bubble enlargement of a segment of the aorta—lateral renal artery bifurcation junction with initial entry of a balloon stent carried within a guide catheter and being advanced over a guide wire;

FIG. 5A is a side cross-sectional view of a balloon stent placement as depicted in FIG. 4A with the stent shown in an accurate position at the aorta renal artery bifurcation junction by a guide catheter marker balloon segment abutted against the aorta bifurcation junction;

FIG. 5B is a bubble enlargement of a segment of the aorta—renal artery bifurcation junction showing a low pressure marker balloon segment abutted against the aorta bifurcation junction for accurate positioning of a bifurcation junction balloon stent;

Figure 8:
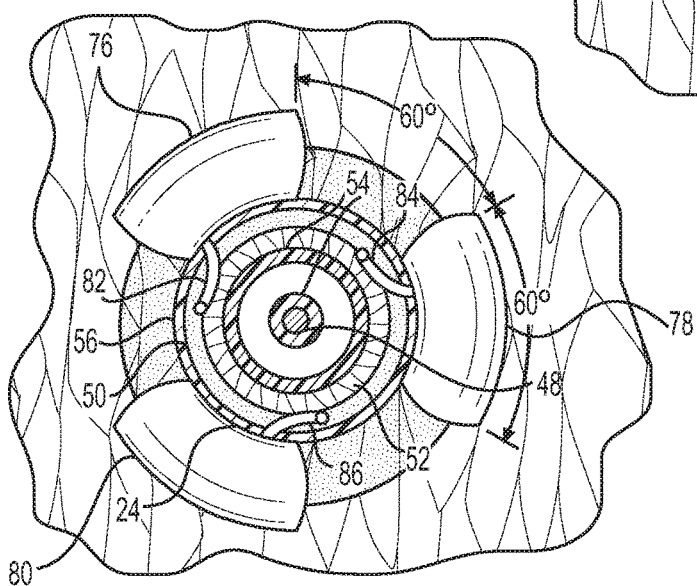
Figure 9A:
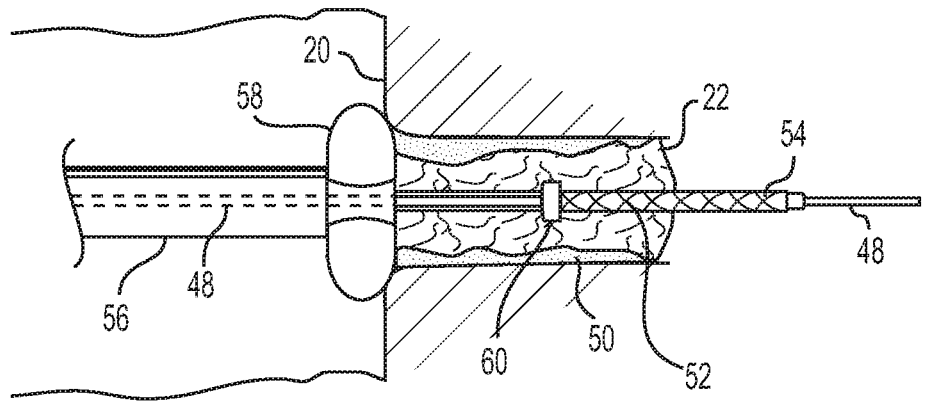
Figure 9B:
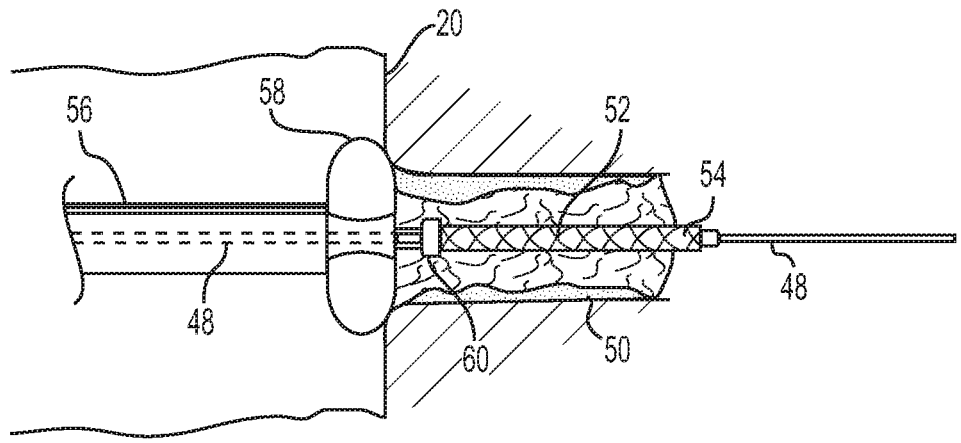
Figure 9C:
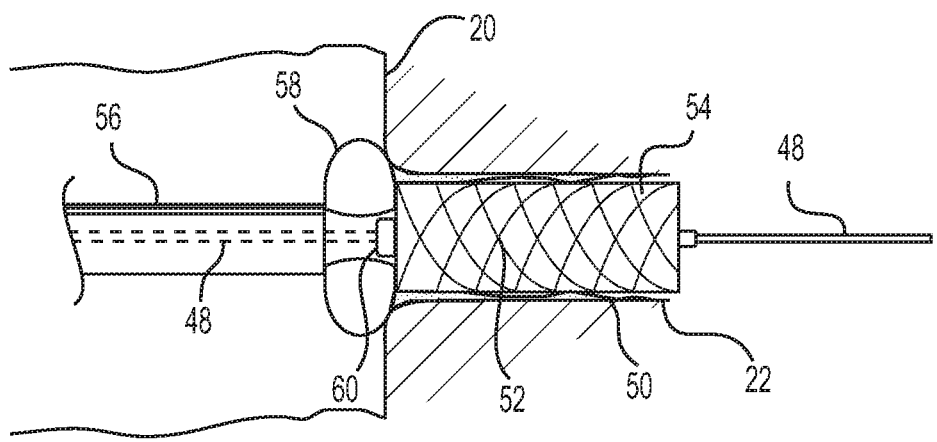

FIG. 8 is an end view and partial cross-sectional view of yet another preferred embodiment of an arcuate, low pressure, marker balloon system of three symmetric segments positioned at a distal end of a guide catheter, at a bifurcation junction of a renal artery with a side wall segment of an aorta; and FIGS. 9A-9C are sequence views disclosing a method of use of the subject guide catheter for angioplasty, with bifurcation stenting sequence for accurate placement of a balloon stent at, for example, a bifurcation junction of an aorta with a renal artery branch.

DETAILED DESCRIPTION

In this description the expression "approximately" or "generally" is intended to mean at or near but not always exactly such that an exact dimension or location is not considered critical in those contexts where those expressions appear. In this description focus will be directed to a guide catheter for angioplasty, with bifurcation stenting, at a renal artery junction with an aorta. This renal artery bifurcation focus, however, is intended to be one of illustration and example and is not intended as a limitation. The subject invention is appropriate and advantageous for most human vascular system bifurcation locations and junctions where a guide catheter finds application.

Figure 1:
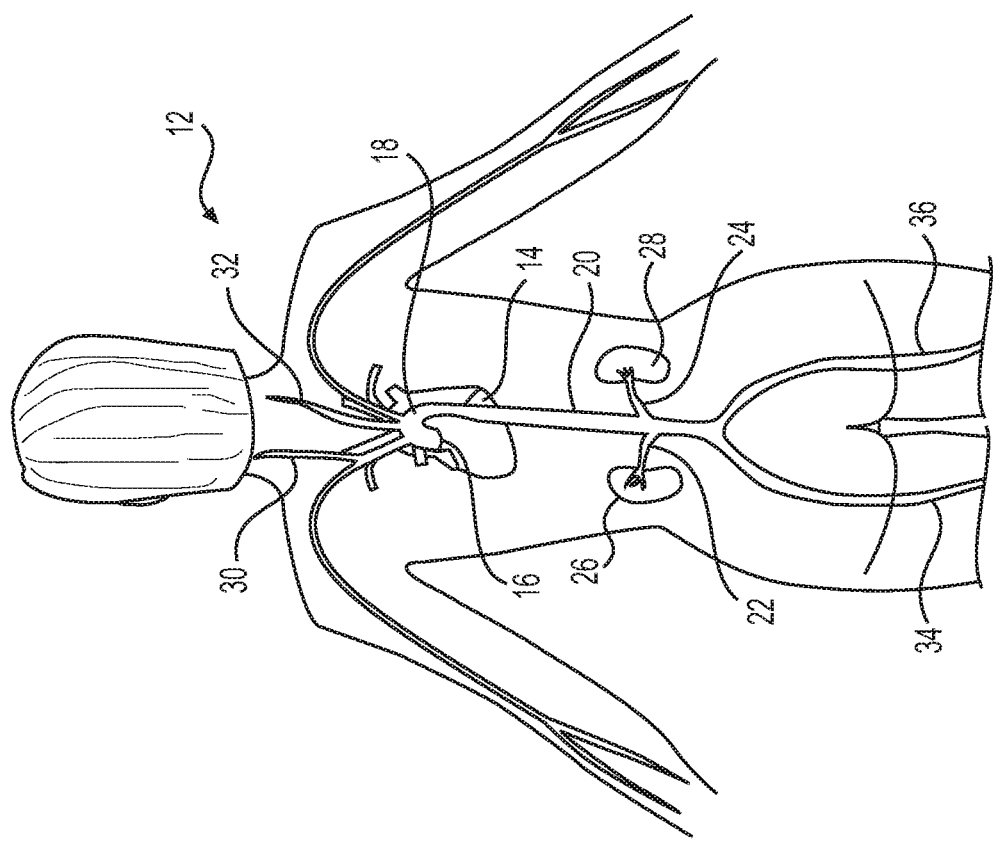
FIG. 1 is an anatomic, silhouette, front view of basic components of a human heart and aorta vascular system.
Figure 2:
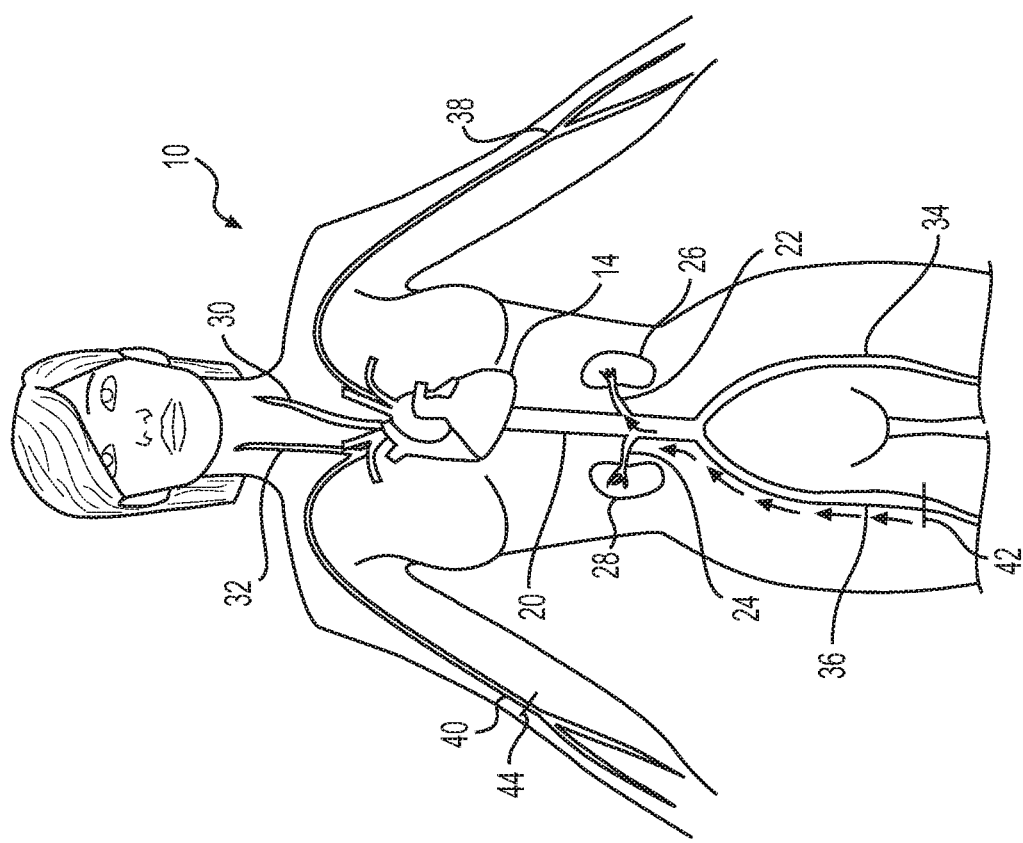
FIG. 2 is an anatomic, silhouette, back view of a similar human heart and aorta vascular system as depicted in FIG. 1.

Turning initially now to FIGS. 1 and 2 there is shown a front 10 and back 12 view of a human figure with outline views of generalized and basic components of a circulatory system with front and back views of a heart 14, an ascending aorta 16 connected to a left ventricle of the heart, an aorta arch 18 and a descending abdominal aorta 20 with renal branch arteries 22 and 24 extending to left and right kidneys 26 and 28 respectively. As indicated above, the human body has a number of arteries stemming from the aorta but for purposes of this description only the renal arteries going to a patient's kidneys are depicted as being representative.

In addition to lateral left and right renal arteries extending from a patient's aorta to a patient's kidneys FIGS. 1 and 2 generally depict left and right carotid arteries 30 and 32 as well as left and right femoral arteries 34 and 36 which bifurcate to superficial femoral and profunda arteries which are illustrative of arteries in a human vascular system. Finally, the FIGURES depict left 38 and right 40 brachial arteries in the figure's arms. A conventional percutaneous entry site for angioplasty, with stenting, is in a patient's common femoral artery at approximately location 42 shown in FIG. 1 or in a brachial arm artery at approximately site 44 also depicted in FIG. 1. Although a renal artery branch is specifically illustrated in the drawings the subject guide catheter with a distal marker balloon segment or balloon segments in addition to use in stenting renal arteries has particular application in other regions of a human circulatory system such as for example stenting an osteal or very proximal stenosis region in a left main coronary artery, a right coronary artery, arteries originating from the aortic arch, iliac arteries at a bifurcation of the abdominal aorta and superficial femoral arteries at a bifurcation of the common femoral arteries.

Figure 3:
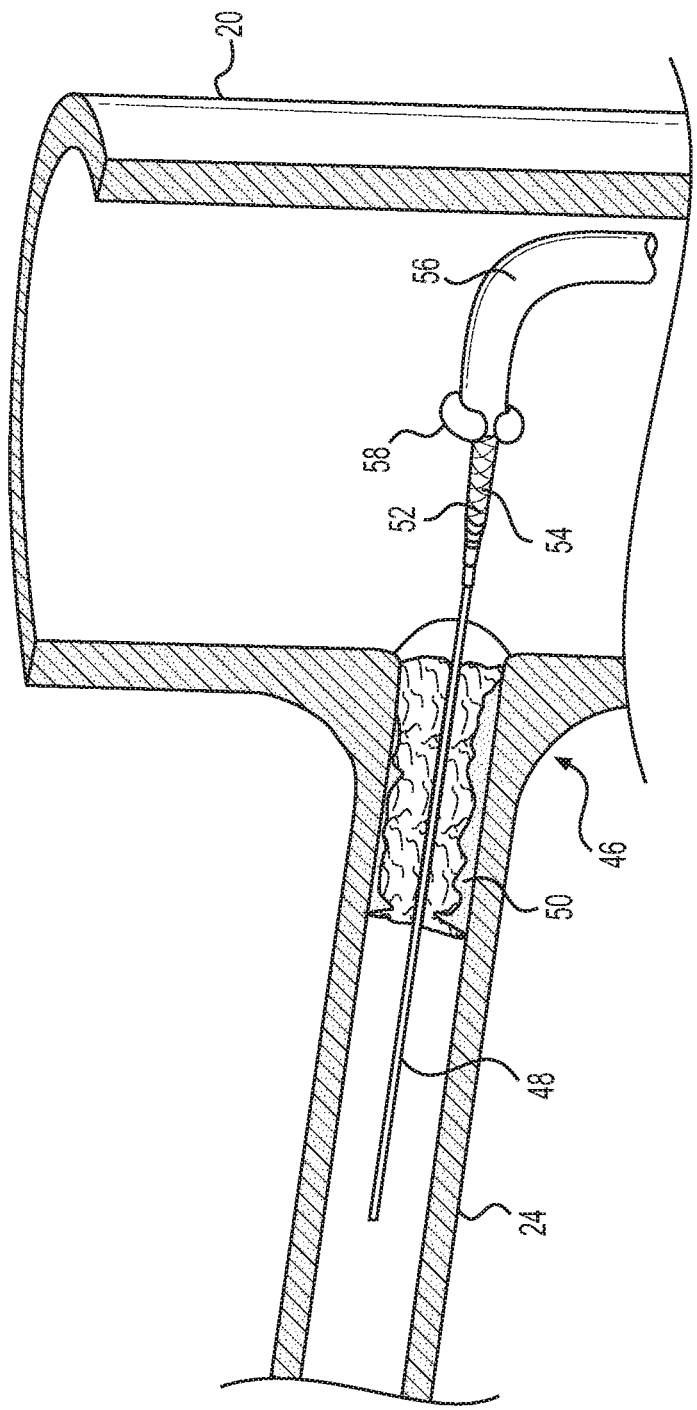
FIG. 3 is axonometric view of an aorta segment and a branch artery, such as a renal artery, for example, extending at essentially a right angle with a plaque stenosis at the aorta branch junction or bifurcation and a guide catheter carrying a guide wire and balloon catheter, with stent, for accurate placement of the stent at the stenosis occlusion.

Referring now to FIG. 3 an aorta 20 is shown in broken away section at a junction location 46 with a renal artery 24, as an example of one specific application of the subject guide and marker catheter. A guide wire 48 is shown extending through the aorta 20 and a plaque stenosis 50. A wire mesh stent 52 surrounds a cylindrical high pressure stent balloon 54. High pressure as used in this disclosure means approximately nine to eighteen atmospheres of pressure. The stent lattice, scaffolding 52 and high pressure stent expansion balloon 54 extends through a guide catheter 56. The stent balloon is generally cylindrical and, is carried along the guide wire 48 to be operably directed by a physician toward the plaque stenotic segment 50 to be treated.

The guide catheter 56 is fitted at a distal end with an arcuate, low pressure, marker balloon segment(s) 58. This marker balloon segment(s) 58 is connected to an inflation tube that extends within the guide catheter 56 to a surgeon's access station. The marker balloon segment(s) 58 can be operably connected to a syringe containing radiopaque marker fluid for injection into the marker balloon segment(s) 58 with a relatively low operating pressure. As used in this description the term low operating pressure means one or two atmospheres of pressure which is low relative to the stent balloon pressure of nine to eighteen atmospheres or more.

In FIG. 4A a wire mesh stent 52 and interior, high pressure, expansion balloon 54 are shown advanced along the guide wire 48 and through the guide catheter 56 to a posture of partial insertion into a lesion zone of a plaque stenosis at a bifurcation junction of the renal artery 24 with the aorta 20.

FIG. 4B is an exploded bubble view of this initial insertion of the balloon stent 52. In this view, an arcuate marker balloon segment 58 is at least partially inflated with a low pressure radiopaque marker fluid at the distal end of the guide catheter 56. This inflation is performed as the guide catheter nears the renal artery bifurcation junction with the aorta 20.

FIG. 5A shows a guide catheter 56 and low pressure marker balloon 58 injected with radiopaque media and positioned adjacent an aorta renal artery bifurcation with a balloon stent 52 extended into a patient stenosis 50 at the bifurcation junction.

Bubble expansion image FIG. 5B illustrates a low pressure marker balloon segment 58 on a distal end of the guide catheter 56 at the renal bifurcation junction and a separate radiopaque band 60 (note FIGS. 9A and 9B), or a separate low pressure stent marker balloon segment at a proximal end of the high pressure stent balloon 54. When the two radiopaque markers 58 and 60 abut into a single radiopaque image the physician is visually alerted to a correct position of a proximal end of the stent at the aorta-renal artery bifurcation location and thus the stent 52 is in an accurate junction location for high pressure expansion of the stent balloon 54 to open the metal stent scaffolding and push the aorta—renal artery junction stenosis 50 outwardly.

Figure 6:
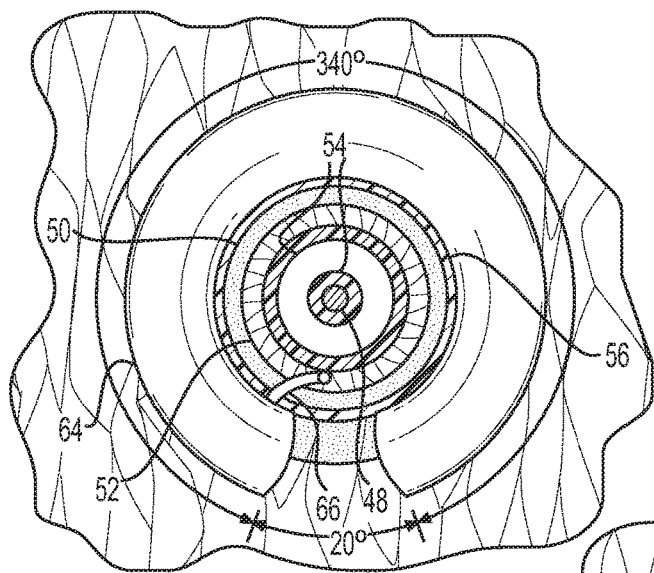
FIG. 6 is an end view and partial cross-sectional view, taken in the direction of arrow "A" in FIG. 5B to disclose interior detail, of one preferred embodiment of an arcuate, low pressure, marker balloon positioned at a distal end of a guide catheter, at a bifurcation junction of a renal artery with a side wall segment of an aorta.

Viewed in the direction of arrow "A" in FIG. 5B, FIG. 6 depicts one preferred embodiment of a single low pressure, arcuate, marker balloon 64 that preferably extends approximately three hundred and forty degrees around a distal end of guide catheter 56. The low pressure, marker balloon segment 64 has a small, low pressure line 66 that extends along or within the guide catheter 56 and is used to inflate the marker balloon segment 64. At a location exterior to a patient's vascular system a physician is able to inject low pressure (one or two atmospheres) radiopaque media into marker balloon 64 by injection from a hand syringe (not shown).

The marker balloon segment 64 preferably occupies an arcuate expanse of approximately three hundred and forty degrees so that there is a minimal gap of at least approximately twenty degrees past the marker balloon for passage of blood through the renal artery during a stenting procedure. Although three hundred and forty degrees is preferred for the arcuate extent of the marker balloon segment 64 a degree of operative advantage can be realized by the subject invention where the arcuate extent of the single marker balloon segment 64 shown in FIG. 6 is as little as forty five degrees.

Figure 7:
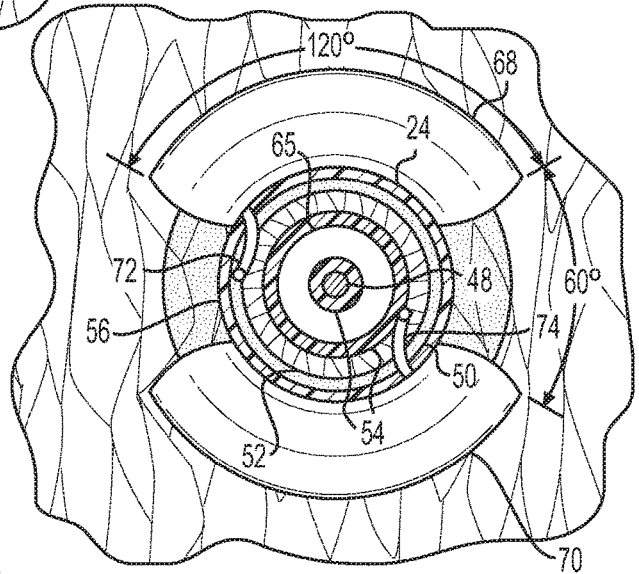
FIG. 7 is an end view and partial cross-sectional view of another preferred embodiment of an arcuate, low pressure, marker balloon system of opposing balloon segments positioned at a distal end of a guide catheter, at a bifurcation junction of a renal artery with a side wall segment of an aorta.

FIG. 7 is a view similar to FIG. 6 but discloses an alternate preferred embodiment of the invention disclosing a low pressure marker balloon system including placement of two arcuate low pressure marker balloon segments 68 and 70 positioned in an opposing posture at a distal end of the guide catheter 56. This balanced arrangement of arcuate marker balloon segments, which can be independently inflated with marker fluid, enhances an ability to establish approximately coaxial placement of the opening of a guide catheter with a branch artery. In this embodiment each of the two balloon segments subtends an angle of at least one hundred degrees but less than one hundred and forty degrees and preferably one hundred and twenty degrees. The substantial open region, of approximately eighty to one hundred and sixty degrees, provides relatively unobstructed blood flow during a stenting procedure.

Each of the marker balloon arcuate segments is fitted with an independent thin tube 72 and 74 extending through the guide catheter for use in separately filling the low pressure marker balloons 68 and 70 respectively with a radiopaque fluid by using a syringe. The capacity to separately inflate each marker balloon enables a physician to selectively orient the end of the guide catheter 56 with respect to a branch artery as necessary or desirable to facilitate a normal or near normal positioning of the end of a guide catheter 56 with respect to placement at a desired branch artery.

FIG. 8 discloses yet another preferred embodiment of the invention including three approximately uniform arcuate marker balloons composed of low pressure balloon segments 76, 78 and 80 and independent fill lines 82, 84 and 86. This enables transmission of a low pressure radiopaque marker media via a syringe to the marker balloon segments at the distal end of the guide catheter 56. The marker balloon segments each extend peripherally around a distal end of the guide catheter at least approximately twenty degrees but less than one hundred degrees and preferably sixty degrees in arcuate extent around a distal end of the guide catheter 56. In this embodiment it is preferred that there is symmetric positioning of the marker balloon segments. This preferred marker balloon spacing concomitantly provides at least approximately sixty degrees of open space for blood flow during a stenting procedure and with three independent pressure zone capacity there is enhanced positioning capability of a distal end of a guide catheter 56 with respect to a branch artery by appropriate selection of pressure within each marker balloon segment.

FIGS. 9A-9C disclose a stenting procedure sequence in accordance with a preferred embodiment of the invention. In this, FIG. 9A depicts a guide wire 48 inserted through a stenosis 50 at a problem bifurcation junction of a renal artery 22 or 24 (note again FIGS. 1 and 2) with an aorta sidewall 20. In FIG. 9A the guide catheter 56 is shown advanced along the guide wire 48 until a low pressure, marker balloon 58 at a distal end of the guide catheter 56 abuts the aorta side wall 20 at the renal artery branch 22.

A syringe is used to inflate the low pressure marker balloon segment or segments 58 with a radiopaque marker media and the guide catheter 56 is positioned against the side wall of the aorta 20 at the renal artery bifurcation site. A balloon stent is slid over the guide wire 48 generally coaxially within the interior of the guide catheter 56 until a radiopaque stent marker 60 is positioned into the region of a bifurcation stenosis 50 as illustrated in FIG. 9A.

In FIG. 9B a physician is operably drawing the balloon stent 52 back along the guide wire 48 until a stent proximal marker 60, or low pressure balloon arcuate segment or segments, such as depicted in FIGS. 6-8, comes into register with a distal end of the guide catheter and the low pressure marker balloon segment or segments 58 at the distal end of the guide catheter 56. In this, the radiopaque image will become essentially one as the proximal end of the stent marker 60 slides into registry with the inflated marker balloon region 58 at a distal end of the guide catheter.

When the radiopaque marker 60 or low pressure marker balloon segment or segments at a proximal end of the balloon stent overlaps with the cover of the guide catheter marker balloon segment or segments 58 a physician accurately knows that a proximal end of the stent 52 is in a proper posture at a bifurcation location of, for example, the aorta—renal artery junction. At this point the interior stent balloon 54 is inflated with approximately nine to eighteen atmospheres of pressure to expand the wire stent scaffolding 52 as shown in FIG. 9C. Once expanded the plaque stenosis 50 is pushed outwardly allowing the damaged site to be enlarged internally to restore a flow of blood through the stenotic site.

The arcuate marker balloon segment gap(s) around the distal end of the guide catheter 56 enables blood perfusion to the diseased branch during accurate positioning of the stent at a bifurcation which may take minutes. The marker balloon segment gap(s) will also allow continuous measuring of blood pressure in the aorta by the guide catheter, when the marker balloon segment or segments are inflated.

When injecting radiopaque media through the guide catheter 56 radiopaque contrast media passes between the marker balloon segment(s) and into the side branch lumen thus providing a view of the downstream side vessel geometry and confirming a desired position of the marker balloon and stent relative to the main vessel and the side branch lumen.

In general the low pressure marker balloon(s) will cover varying degrees of the blood vessel opening, and the degree of coverage and marker balloon pressure may vary to allow matching the branching angle, such as when positioning the stent at a bifurcation that is less than 90 degrees. This might occur at the bifurcation of the abdominal aorta into the iliac arteries and the bifurcation of the common femoral arteries. In these instances the interventional physician, may prefer a marker balloon extending less than one hundred and eight degrees, in a way that the marker balloon will fall on the shoulder of the bifurcation, rather in the lumen of the branching vessel.

The low pressure marker balloon segment or segments outer cross sectional diameter is smaller the diameter of the main artery, to allow proper inflation, however, the cross sectional diameter is larger than a diameter of the side branch, in a way that prevents a prolapse into the side branch. In this connection, and as an example, the outside diameter of the marker balloon segment or segments should be between four and ten millimeters to butt against a junction location of an artery with the aorta side wall. The longitudinal extent of the catheter marker balloon segment or segments, when inflated, should reach but not unduly impinge upon the expanded stent.

The advantages provided by a low pressure marker balloon segment or segments mounted on a distal end of a guide catheter facilitates, for example, accurate positioning of a stent downstream of the aorta side wall and into a patient's branch vascular system. In this context the low pressure balloon market segment or segments permits both a flow of blood during a downstream stenting procedure and also a flow of radiopaque marker media to facilitate accurate placement of a stent at a downstream stenosis site. Although the structure of a low pressure marker balloon segment (or segments) are depicted, for example, in FIGS. 6-8, it will be appreciated by those skilled in the art that the physical size of the arcuate marker balloon segment, and arcuate marker balloon segments, in certain instances, may be selected to suit the anatomy of a patient of interest.

In describing the invention, reference has been made to preferred embodiments. Those skilled in the art however, and familiar with the disclosure of the subject invention, may recognize additions, deletions, substitutions, modifications and/or other changes which will fall within the scope of the invention as defined in the following claims.

What is claimed is:

1. An angioplasty marker and catheter apparatus for facilitating accurate placement of a stent for dilating a stenotic segment at a lumen bifurcation junction, said angioplasty marker and catheter apparatus comprising: a marker balloon assembly having a proximal end and a distal end, said assembly including, a guide wire and a tubular conduit, the marker balloon assembly configured to slide back and forth over the guide wire, the marker balloon assembly connected to a distal end of said tubular conduit, said marker balloon assembly including at least one inflatable marker balloon segment, said at least one inflatable marker balloon segment having an arcuate, circumferential extent less than or equal to three hundred forty degrees about the distal end of said tubular conduit, and an inflation conduit connected to said tubular conduit and being operable to be connected to an inflation syringe at a proximal end of said marker balloon assembly and to said at least one inflatable marker balloon segment mounted at the distal end of said tubular conduit for selective delivery of marker fluid under low pressure to said at least one inflatable marker balloon segment and a stent catheter assembly operable to be inserted through said marker balloon assembly, said stent catheter assembly further comprising a radio-opaque stent proximal marker positioned at a proximal end of the stent, said stent catheter assembly operable to be advanced or drawn back along the guide wire so that a stent position is determinable by an operator viewing a radio image showing a relative position of the radio-opaque stent marker and the marker balloons.

2. The angioplasty marker and catheter apparatus for facilitating accurate placement of the stent for dilating the stenotic segment at the lumen bifurcation junction as defined in claim 1 wherein said marker balloon assembly having at least one inflatable segment comprises: an arcuate shaped balloon segment mounted at a distal end of said marker balloon assembly, said arcuate shaped balloon segment subtends an arc of at least forty five degrees.

3. The angioplasty marker and catheter apparatus for facilitating accurate placement of the stent for dilating the stenotic segment at the lumen bifurcation junction as defined in claim 1 wherein said marker balloon assembly having at least one marker balloon segment comprises: at least two independent and symmetrically opposing arcuate shaped balloon segments mounted at the distal end of said maker balloon assembly.

4. The angioplasty marker and catheter apparatus for facilitating accurate placement of the stent for dilating the stenotic segment at the lumen bifurcation junction as defined in claim 3 wherein: each of said two independent and symmetrically opposing arcuate shaped marker balloon segments mounted at the distal end of said marker balloon assembly subtends an arc of at least approximately one hundred degrees but less than approximately one hundred and forty degrees.

5. The angioplasty marker and catheter apparatus for facilitating accurate placement of the stent for dilating the stenotic segment at the lumen bifurcation junction as defined in claim 3 wherein: each of said two independent and symmetrically opposing arcuate marker balloon segments mounted at the distal end of said marker balloon assembly subtends an arc of at least approximately one hundred twenty degrees.

6. The angioplasty marker and catheter apparatus for facilitating accurate placement of the stent for dilating the stenotic segment at the lumen bifurcation junction as defined in claim 1 wherein said marker balloon assembly having at least one inflatable marker balloon segment comprises: an arcuate marker balloon segment mounted at the distal end of said marker balloon assembly, said arcuate marker balloon segment subtends an arc of at least approximately forty five degrees.

7. The angioplasty marker and catheter apparatus, for facilitating accurate placement of the stent for dilating the stenosis at the bifurcation as defined in claim 1 wherein said marker balloon having at least one inflatable marker balloon segment comprises: at least two independent and symmetrically opposing arcuate marker balloon segments mounted at a distal end of said marker balloon assembly subtends an arc of approximately one hundred and forty degrees.

* * * * *